(12) United States Patent
Zhang et al.

(10) Patent No.: US 11,225,504 B2
(45) Date of Patent: Jan. 18, 2022

(54) FUNCTIONAL POLYPEPTIDE AND ITS APPLICATION THEREOF IN PREPARING MEDICAMENT FOR PREVENTING AND TREATING PULMONARY FIBROSIS

(71) Applicant: Guangdong Medical University, Zhanjiang (CN)

(72) Inventors: Haitao Zhang, Zhanjiang (CN); Huajun Yu, Zhanjiang (CN); Jun Wu, Zhanjiang (CN); Hui Luo, Zhanjiang (CN)

( * ) Notice: Subject to any disclaimer, the term of this patent is extended or adjusted under 35 U.S.C. 154(b) by 262 days.

(21) Appl. No.: 16/331,995

(22) PCT Filed: Jun. 16, 2018

(86) PCT No.: PCT/CN2018/091731
§ 371 (c)(1),
(2) Date: Mar. 11, 2019

(87) PCT Pub. No.: WO2019/095685
PCT Pub. Date: May 23, 2019

(65) Prior Publication Data
US 2021/0047370 A1 Feb. 18, 2021

(30) Foreign Application Priority Data
Nov. 17, 2017 (CN) .......................... 201711141671.X

(51) Int. Cl.
*C07K 7/08* (2006.01)
*A61P 11/00* (2006.01)
*A61K 38/00* (2006.01)

(52) U.S. Cl.
CPC ................ *C07K 7/08* (2013.01); *A61P 11/00* (2018.01); *A61K 38/00* (2013.01)

(58) Field of Classification Search
CPC ........... C07K 7/08; A61K 38/00; A61K 38/10
See application file for complete search history.

(56) References Cited

FOREIGN PATENT DOCUMENTS

| | | |
|---|---|---|
| CN | 105263948 A | 1/2016 |
| CN | 106913858 A | 7/2017 |
| CN | 107987128 A | 5/2018 |
| CN | 108329381 A | 7/2018 |
| WO | WO 2019095685 | * 5/2019 |

OTHER PUBLICATIONS

"Amino Acids reference charts", https://www.sigmaldrich.com/life-science-metabolomics/learning-center/amino-acid-reference-chart.html, 1991, accessed Apr. 21, 2021 (Year: 1991).*
STN CAS Registry: Exact and pattern searching of protein sequences, 2008, p. 12 (Year: 2008).*
Loomis-King. Current Opinion in Pharmacology, 2013, 13, 377-385 (Year: 2013).*
ISA; State Intellectual Property Office of the P.R. China; Beijing China; Aug. 7, 2018.

* cited by examiner

*Primary Examiner* — Noble E Jarrell
(74) *Attorney, Agent, or Firm* — Patshegen IP LLC; Moshe Pinchas

(57) ABSTRACT

The present invention discloses a functional polypeptide which is 1) a polypeptide having the amino acid sequence of SEQ ID No. 1; or 2) a polypeptide having a substitution or deletion or addition of one or several amino acids from the sequence shown in SEQ ID No. 1 that has the same or similar function. The invention also discloses the utility of the described functional polypeptide. The functional polypeptide of the present invention can significantly inhibit bleomycin-induced pulmonary fibrosis formation and has a remarkable effect of preventing and treating pulmonary fibrosis.

10 Claims, 2 Drawing Sheets
Specification includes a Sequence Listing.

FUNCTIONAL POLYPEPTIDE AND ITS APPLICATION THEREOF IN PREPARING MEDICAMENT FOR PREVENTING AND TREATING PULMONARY FIBROSIS

TECHNICAL FIELD

The current invention belongs to the technical field of medicine, and particularly relates to a functional polypeptide and its application thereof in preparing a medicament for preventing and treating pulmonary fibrosis.

TECHNOLOGY BACKGROUND

Idiopathic pulmonary fibrosis (IPF) is a pulmonary interstitial inflammatory disease with unknown causes. In the 2011 International Guidelines for the Diagnosis and Treatment of IPF, IPF is defined as: a chronic, progressive, and fibrotic interstitial pneumonia, with histology and (or) high-resolution chest CT characteristic of Usual Interstitial Pneumonia (UIP). The main pathological feature of IPF is a mixed co-existence of interstitial and alveolar fibrosis and infiltration of inflammatory cells, with progression to terminal respiratory failure or death within 3 to 8 years after the presentation of symptoms. The etiology and pathogenesis of IPF have not yet been fully elucidated and there is a lack of effective therapeutic drugs and objective and informative prognostic indicators. Corticosteroids or immunosuppressants, cytotoxic drugs are still the main treatment for IPF, but only less than 30% of patients have a therapeutic response, while those drugs show toxic side effects. For the treatment of IPF, the Guidelines suggest that the vast majority of patients should not be treated with glucocorticoids, cyclosporine A, colchicine, IFN-β, bosentan or etanercept, nor do they recommend a combination therapy of glucocorticoids and immunosuppressants.

The European Union, Japan, Canada, and China have approved the use of pirfenidone for the treatment of IPF, which is currently used to treat mild to moderate IPF. Although pirfenidone has also been approved, there is still some controversy about the treatment of idiopathic pulmonary fibrosis (IPF) using pirfenidone, and the pirfenidone treatment is associated with side effects such as photosensitivity, anorexia, dizziness, elevated levels of transaminase, eczema, abdominal discomfort, and decreased counts of white blood cells, etc. In 2015, the American Thoracic Society (ATS)/European Respiratory Society (ERS)/Japan Respiratory Society (JRS)/Latin American Thoracic Association (ALAT) collectively recommend in the IPF treatment clinical practice guidelines the use of pirfenidone for IPF patients based on certain conditions and intermediate level evidences. Rationale and considerations during implementation: The adverse reactions of pirfenidone are broad; even with the estimated treatment benefits by FVC evaluation; some patients still can't tolerate certain kind of adverse reactions. Therefore, patients should be educated about adverse reactions before starting the treatment. In addition, the current cost of treatment with pirfenidone is high, so this factor must be taken into consideration when making treatment decisions, especially when the patient is directly responsible for the economic burden of treatment. The price of pirfenidone is high in both Europe and Japan. Although this drug has been used clinically, its effect on improving the symptoms or quality of life of patients with IPF and reducing patient mortality is limited. In the future, it is still needed to make definitive conclusions through clinical observations in countries and regions where piraridone is marketed. Therefore, finding new effective drugs for prevention and treatment of IPF remain a hot area in drug research at home and abroad.

SUMMARY OF THE INVENTION

In order to overcome the deficiencies of the prior art, the present invention aims to provide a functional polypeptide; it can significantly inhibit bleomycin-induced pulmonary fibrosis formation, and has a remarkable effect of preventing and treating pulmonary fibrosis.

In order to solve the above problems, the technical solution adopted by the present invention is as follows:
a functional polypeptide which is
1) a polypeptide having the amino acid sequence of SEQ ID No. 1; or
2) a polypeptide having a substitution or deletion or addition of one or several amino acids from the sequence shown in SEQ ID No. 1 that has the same or similar function.

As a further solution, the present invention and the described functional polypeptide is a derivative with one or more amino group substitutions at the number 1, 2, 8, 9, 11, 13, and 14 positions of the amino acid sequence shown in SEQ ID No. 1 with the same or similar functional amino groups.

The invention also provides a nucleotide sequence encoding to the above described functional polypeptide sequence.

The invention also provides a vector containing the above described nucleotide sequence.

The invention also provides a host cell containing the above described vector.

The invention also provides the utility of the above described functional polypeptide, which can be used for preparing a medicament for preventing and treating pulmonary fibrosis, or as an active ingredient for drugs preventing and treating pulmonary fibrosis, or using the functional polypeptide as an optimizable precursor for preventing and treating pulmonary fibrosis, or combination with drugs treating pulmonary fibrosis. The specific plan is as follows:

The use of the above described functional polypeptide in the preparation of a medicament for the prevention and treatment of pulmonary fibrosis.

The use of the above described functional polypeptide as an active ingredient for the drugs of prevention and treatment of pulmonary fibrosis.

The use of the above described functional polypeptide as of an optimizable precursor for preventing and treating pulmonary fibrosis.

The use of the above described functional polypeptide in combination with pirfenidone for the preparation of a medicament for preventing and treating pulmonary fibrosis.

A medicament for the treatment of pulmonary fibrosis, containing the polypeptides described in the invention.

Compared with prior arts, the beneficial effects of the present invention are:

1. The functional polypeptide of the present invention has a good effect of preventing and treating IPF, and the levels of hydroxyproline (HYP) in the lung tissue and malondialdehyde (MDA) in the plasma were significantly reduced; plasma levels of total superoxide dismutase (T-SOD) and glutathione peroxidase (GSH-PX) were significantly increased;

2. The functional polypeptide of the present invention can be used to prepare a medicament, an active ingredient or a prodrug of a drug for preventing and treating IPF;

3. The medicine or health care products for preventing and treating pulmonary fibrosis containing the functional polypeptide described in the present invention can be formulated as a powder or an injection or an oral product, and can be used as a final product alone or as an active ingredient to compound with physiological saline solution, glucose solution or other adjuvant solutions, and can also be used in combination with drugs currently used for treating pulmonary fibrosis.

The present invention will be further described in detail below in conjunction with the drawings and specific embodiments.

DRAWINGS

SPECIFIC EMBODIMENTS

Figure 1:
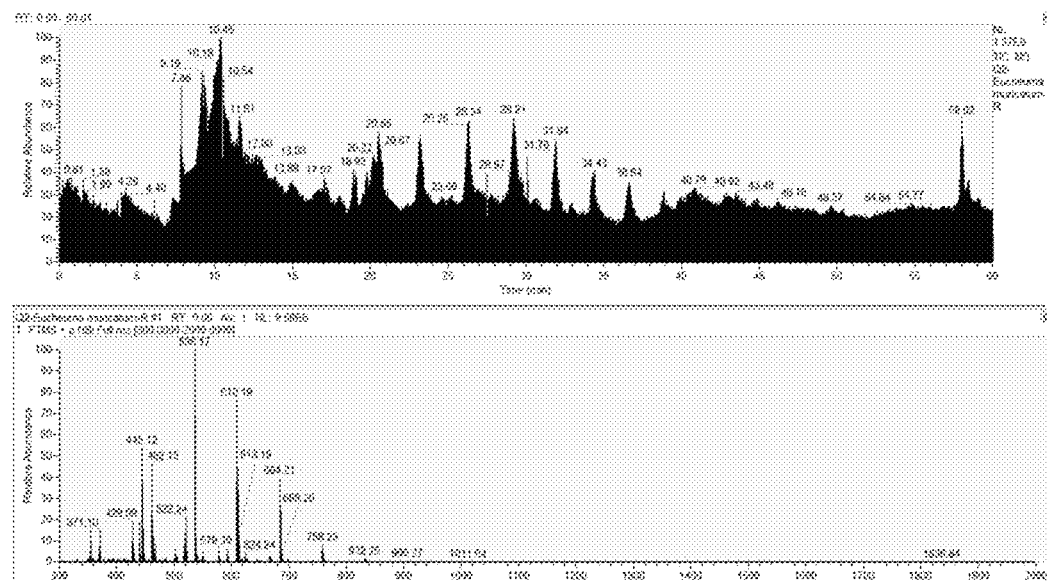
FIG. 1 is the LC-MS/MS structural analysis of the functional polypeptide of the present invention.

The present invention provides a functional polypeptide which is 1) a polypeptide having the amino acid sequence of SEQ ID No. 1; or 2) a polypeptide having a substitution or deletion or addition of one or several amino acids from the sequence shown in SEQ ID No. 1 that has the same or similar function.

Wherein the sequence of SEQ ID No. 1 is RTGACFCVIYNGILYP.

As a further solution, the present invention and the described functional polypeptide is a derivative with one or more amino group substitutions at the number 1, 2, 8, 9, 11, 13, and 14 positions of the amino acid sequence shown in SEQ ID No. 1 with the same or similar functional amino groups. Specifically, it may be selected, but not limited to, one or more of the following substitutions: the first amino acid R in the sequence of SEQ ID No. 1 is replaced with a K amino group, since R and K are both basic amino acids, with similar functions; the second amino acid T is replaced by the amino acid S, because T and S are both hydroxyl-containing amino acids, with similar functions; the eighth amino acid V is replaced by amino I or L, for the reason that V, I and L are all branched-chain amino acids, with similar functions; the 9th amino acid I is replaced by V or L, on the grounds that V, I and L are both branched-chain amino acids, with similar functions; The amino acid N at position 11 is replaced by Q, because N and Q are both proaminoamide group-containing amino acids, with similar functions; the 13th amino acid I is replaced by V or L, for the reason that V, I and L are all the same branched-chain amino acids, with similar functions; the 14th amino acid L is replaced by V or I, on the grounds that V, I and L are all branched-chain amino acids, with similar functions.

The invention also provides a nucleotide sequence encoding to the above described functional polypeptide sequence.

The invention also provides a vector containing the above described nucleotide sequence.

The invention also provides a host cell containing the above described vector.

The invention also provides the utility of the above described functional polypeptide, which can be used for preparing a medicament for preventing and treating pulmonary fibrosis, or as an active ingredient for drugs preventing and treating pulmonary fibrosis, or using the functional polypeptide as an optimizable precursor for preventing and treating pulmonary fibrosis, or combination with drugs treating pulmonary fibrosis. The specific plan is as follows:

The use of the above described functional polypeptide in the preparation of a medicament for the prevention and treatment of pulmonary fibrosis.

The use of the above described functional polypeptide as an active ingredient for the drugs of prevention and treatment of pulmonary fibrosis.

The use of the above described functional polypeptide as of an optimizable precursor for preventing and treating pulmonary fibrosis.

The use of the above described functional polypeptide in combination with pirfenidone for the preparation of a medicament for preventing and treating pulmonary fibrosis.

The functional polypeptide compound of the present invention can be used in the prevention and treatment of IPF in the following ways:

Method 1: The functional polypeptide compound of the present invention is orally administered at a dose of 1 to 10 mg/kg once a day for at least 35 days.

Method 2: The functional polypeptide compound of the present invention is injected from 0.1 to 1 mg/kg once every three days for at least 35 days.

Method 3: In combination with drugs currently used for treating IPF (for example, pirfenidone), the EZY-1 polypeptide compound is administered orally in an amount of 1 to 10 mg/kg once a day.

A medicament for the treatment of pulmonary fibrosis contains the polypeptide described in the present invention.

The following are specific examples of the present invention, and the materials, reagents and the like used in the following examples are all prior art, except those specifically defined in the present invention.

The functional polypeptide described in the present invention can be synthesized using amino acids as raw materials by polypeptide synthesis equipment according to the amino acid sequence of SEQ ID No. 1, and purified by high performance liquid chromatography. The product can be tested; the results are shown in FIGS. 1-4.

Figure 2:
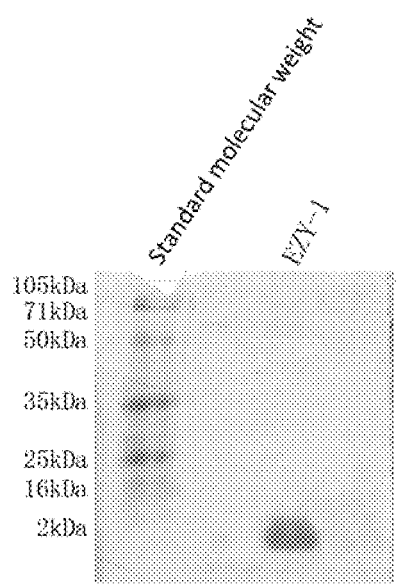
FIG. 2 is a graph showing the analysis results by SDS-PAGE electrophoresis of the functional peptide of the present invention.
Figure 3:
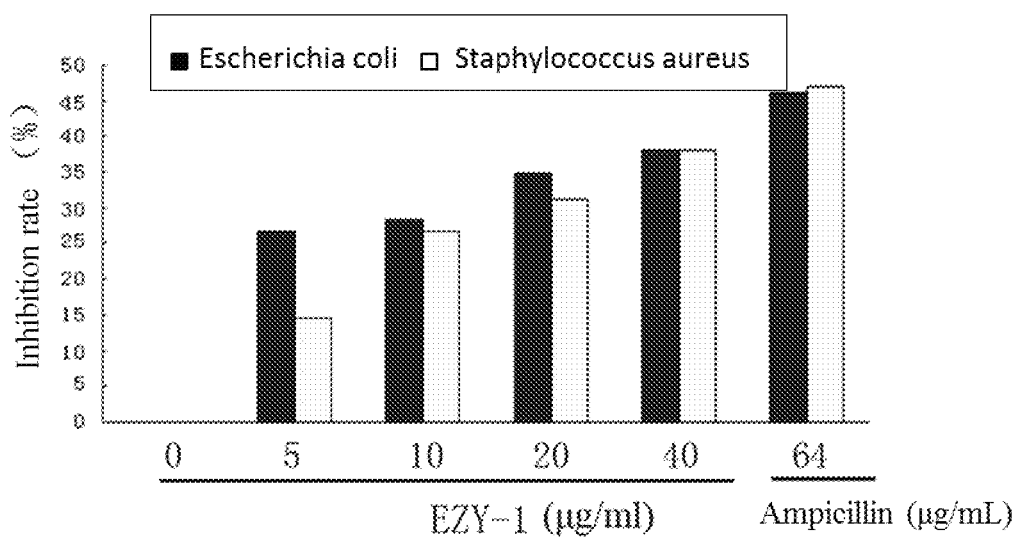
FIG. 3 is a graph showing the analysis results of the anti-bacterial activity of the functional polypeptide of the present invention.
Figure 4:
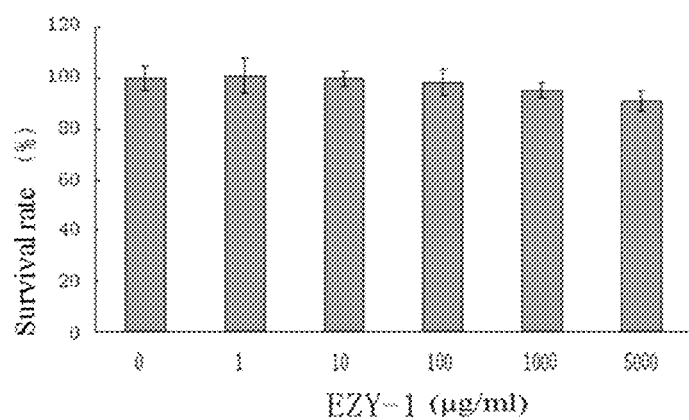
FIG. 4 is a graph showing the growth effects of the functional polypeptide of the present invention on human normal lung epithelial cell BEAS-2B.

FIG. 1 is the LC-MS/MS structural analysis of the functional polypeptide of the present invention; FIG. 2 is a graph showing the analysis results by SDS-PAGE electrophoresis of the functional peptide of the present invention; FIG. 3 is a graph showing the analysis results of the anti-bacterial activity of the functional polypeptide of the present invention. The result shows that the functional polypeptide has a certain bacteriostatic effect; FIG. 4 is a graph showing the growth effects of the functional polypeptide of the present invention on human normal lung epithelial cell BEAS-2B and the results show that the functional polypeptide of the present invention has low toxicity to normal cells.

Prevention and treatment of pulmonary fibrosis IPF experiment

1. Experimental Methods (1) Animals: SPF grade C57 mice, 22 g±2 g, 60 mice, females.

(2) Grouping

The mice was divided into the following groups using the random digits table: the control group, the model group, the pirfenidone group (50 mg/kg), the EZY-1 polypeptide low dose group (0.25 mg/kg), the EZY-1 polypeptide medium dose group (0.5 mg/kg), the EZY-1 polypeptide high dose group (1.0 mg/kg), 10 animals per group.

(3) After the mice were anesthetized by intraperitoneal injection of 1% sodium pentobarbital at a dose of 50 mg/kg, they are fixed to the operation console on their back. Their tongues were pulled out with tweezers to expose the trachea, and 5 mg/kg Bleomycin was slowly injected under a cold light source magnifying glass. Immediately after the injection, the operation console was erected and rotated for 3 minutes to evenly distribute the drug solution in the lungs.

The control group was injected with an equal volume of isotonic saline in the same way as the previous method. After 10 days, the mice were intra-gastrically administered with 0.1 ml/10 g with drugs. The control group and the model group were intra-gastrically administered with an equal volume of isotonic saline. The other groups were intra-gastrically administered with the corresponding dose of the drug for 35 days, once a day.

(4) Tissue harvest and measurement of indicators:

After 35 days of drug administration, the mice were anesthetized and sacrificed, and the two intact lung tissues were isolated and weighed. The same part of the right upper lobe was taken, fixed with 4% paraformaldehyde for 48 hours, and paraffin sections were generated for Hematoxylin-Eosin (HE) staining for histopathological observations.

The same part of the left middle lobe was taken for the measurement of HYP content in the lung tissue.

Plasma was collected for the measurement of T-SOD, MDA, and GSH-PX levels. Statistical analysis was performed using SPSS 17.0 software. Measurement data were expressed as mean±standard deviation ($\bar{x}\pm s$). Comparison of the means in multiple samples was performed by one-way ANOVA. Comparison between groups was performed by t test, with $P \leq 0.05$ indicating statistically significant differences.

2, Results (1) Analysis of HYP Content in Mouse Lung Tissues

The content of hydroxyproline (HYP) in the lung tissue of each group ($\bar{x}\pm s$) was higher than that in the control group (P<0.01). Compared with the model group, the HYP content in each treated group was significantly lower (P<0.01). See Table 1.

(2) Analysis of plasma T-SOD, MDA, GSH-PX levels in mice, and the results are shown in Table 1.

The results in Table 1 showed that plasma T-SOD, MDA, GSH-PX levels ($\bar{x}\pm s$) in each group. Compared with the control group, plasma MDA levels increased (P<0.01) in the model group and the low, medium and high-dose groups. Compared with the control group, plasma T-SOD and GSH-PX levels decreased in each other group (P<0.01). Compared with the model group, the plasma MDA levels of each group was significantly decreased (P<0.01). Compared with the model group, the plasma T-SOD and GSH-PX levels of each group increased (P<0.01).

TABLE 1

Comparison of biochemical indicators in each group

| Group | HYP (μg/g lung tissues Wet weight) | T-SOD (U/mL) | MDA (nmal/mL) | GSH-PX (active unit) |
|---|---|---|---|---|
| The control group | 17.08 ± 1.23 | 180.98 ± 5.96 | 3.92 ± 0.34 | 1102.01 ± 72.23 |
| The Model group | 85.36 ± 5.85*# | 85.28 ± 13.67*# | 25.42 ± 5.64*# | 349.99 ± 22.51*# |
| The EZY-1 polypeptide low dose group (0.25 mg/kg) | 67.82 ± 6.18*# | 128.06 ± 12.75*# | 16.63 ± 5.02*# | 462.56 ± 68.17*# |
| The EZY-1 polypeptide medium dose group (0.5 mg/kg) | 62.80 ± 9.75*# | 138.04 ± 7.36*# | 9.88 ± 0.92*# | 612.56 ± 20.63*# |
| The EZY-1 polypeptide high dose group (1.0 mg/kg) | 58.66 ± 7.17*# | 140.75 ± 18.58*# | 7.96 ± 0.69*# | 728.83 ± 38.52*# |
| The pirfenidone group (50 mg/kg) | 48.36 ± 5.01*# | 156.05 ± 17.32*# | 6.52 ± 0.71*# | 672.92 ± 98.72*# |

Compared with the control group: *P < 0.01;
Compared with the model group: #P < 0.01.

The results in Table 1 show that the functional polypeptide of the present invention can alleviate collagen fiber deposition and inhibit pulmonary fibrosis.

Figure 5:
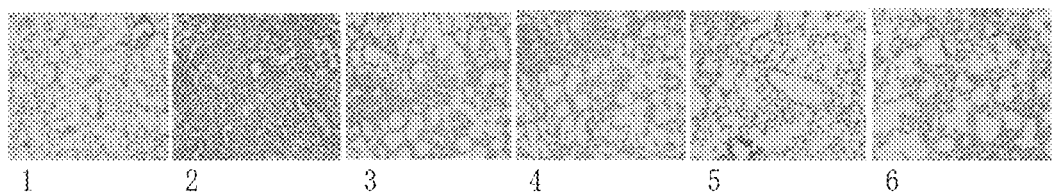
FIG. 5 is a graph showing the results of HE staining (×200) of mouse lung tissue sections in the IPF inhibition experiment by EZY-1 polypeptide; wherein, 1. control group; 2. model group; 3. 0.25 mg/kg EZY-1 polypeptide dose group; 4. 0.5 mg/kg EZY-1 polypeptide dose group; 5. 1.0 mg/kg EZY-1 polypeptide dose group; 6. 50 mg/kg pirfenidone dose group.

(3) Analysis of pathological changes of lung tissue, the results are shown in FIG. 5.

As shown in FIG. 5, the lung structure of the control group was clear, while the alveolar space of the model group was significantly widened and the alveolar structure was severely damaged and there is severe atrophy collapse, dramatically increased collagen fibers, and infiltration of a large number of inflammatory cells. The low, medium and high dose groups of EZY-1 peptide and pirfenidone treated group can reduce alveolar structural damage, reduce collagen fiber production, and inhibit the inflammatory cell infiltration. This demonstrates that the drug treatment gradually reduced pulmonary fibrosis.

The above embodiments are merely preferred embodiments of the present invention, and the scope of the present invention is not limited thereto. Any insubstantial changes and substitutions made by those skilled in the art based on the present invention belong to the scope of the present invention.

The invention claimed is:

1. A functional polypeptide, which is a polypeptide having the amino acid sequence of SEQ ID No. 1.

2. A functional polypeptide wherein said functional polypeptide is a derivative with one or more amino group substitutions at the number 1, 2, 8, 9, 11, 13, and 14 positions of the amino acid sequence shown in SEQ ID No. 1, wherein: arginine at position 1 can be substituted with lysine; threonine at position 2 can be substituted with serine; valine at position 8 can be substituted with isoleucine or leucine; isoleucine at position 9 can be substituted with valine or leucine; asparagine at position 11 can be substituted with glutamine; isoleucine at position 13 can be substituted with valine or leucine; and leucine at position 14 can be substituted with valine or isoleucine.

3. A method of treating pulmonary fibrosis in a subject in need thereof, comprising administering to the subject the functional polypeptide of claim 1.

4. The method of claim 3, wherein said functional polypeptide is an active ingredient for treating pulmonary fibrosis.

5. The method of claim 3, wherein said functional polypeptide is administered in combination with pirfenidone.

6. A medicament for the treatment of pulmonary fibrosis, comprising the functional polypeptide of claim 1.

7. A method of treating pulmonary fibrosis in a subject in need thereof, comprising administering to the subject the functional polypeptide of claim 2.

8. The method of claim 7, wherein said functional polypeptide is an active ingredient for treating pulmonary fibrosis.

9. The method of claim 7, wherein said functional polypeptide is administered in combination with pirfenidone.

10. A medicament for the treatment of pulmonary fibrosis, comprising the functional polypeptide of claim 2.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: artificial
<220> FEATURE:
<223> OTHER INFORMATION: preventing and treating pulmonary fibrosis

<400> SEQUENCE: 1

```
Arg Thr Gly Ala Cys Phe Cys Val Ile Tyr Asn Gly Ile Leu Tyr Pro
1               5                   10                  15
```